(12) United States Patent
Kolodka et al.

(10) Patent No.: US 8,044,022 B2
(45) Date of Patent: Oct. 25, 2011

(54) HYALURONIC ACID BINDING PEPTIDES ENHANCE HOST DEFENSE AGAINST PATHOGENIC BACTERIA

(76) Inventors: Tadeusz Kolodka, Manitoba (CA); Bernard T. Charlton, Manitoba (CA); Wendy Johnson, Manitoba (CA)

( * ) Notice: Subject to any disclaimer, the term of this patent is extended or adjusted under 35 U.S.C. 154(b) by 642 days.

(21) Appl. No.: 11/917,012

(22) PCT Filed: Jun. 8, 2006

(86) PCT No.: PCT/CA2006/000929
§ 371 (c)(1), (2), (4) Date: Jul. 31, 2008

(87) PCT Pub. No.: WO2006/130974
PCT Pub. Date: Dec. 14, 2006

(65) Prior Publication Data
US 2009/0030180 A1 Jan. 29, 2009

Related U.S. Application Data

(60) Provisional application No. 60/688,343, filed on Jun. 8, 2005, provisional application No. 60/733,807, filed on Nov. 7, 2005.

(51) Int. Cl.
| | | |
|---|---|---|
| *A01N 37/18* | (2006.01) | |
| *A61K 38/04* | (2006.01) | |
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl. .................... 514/2.6; 514/2.7; 530/324
(58) Field of Classification Search .................. None
See application file for complete search history.

(56) References Cited

U.S. PATENT DOCUMENTS

| 5,916,872 A | * | 6/1999 | Chang et al. .................. 514/2.6 |
| 6,448,224 B1 | * | 9/2002 | Novak et al. .................. 514/2.4 |
| 2002/0155455 A1 | | 10/2002 | Tadayoni-Rebek et al. |
| 2010/0316643 A1 | * | 12/2010 | Eckert et al. ............... 424/134.1 |
| 2011/0039761 A1 | * | 2/2011 | Eckert et al. .................. 514/2.4 |
| 2011/0039762 A1 | * | 2/2011 | Eckert et al. .................. 514/2.4 |
| 2011/0039763 A1 | * | 2/2011 | Eckert et al. .................. 514/2.4 |

FOREIGN PATENT DOCUMENTS

| EP | 950708 | 10/1999 |
| WO | WO97/24111 | 10/1997 |
| WO | WO01/80899 | 11/2001 |
| WO | WO02/28415 | 11/2002 |

OTHER PUBLICATIONS

Lee et al. Modulation of the Local Neutrophil Response by a Novel Hyaluronic Acid-Binding Peptide Reduces Bacterial Burden during Staphyloccal Wound Infection. Infection and Immunity, Oct. 2010. vol. 78, No. 10, pp. 4176-4186.*

* cited by examiner

*Primary Examiner* — Marcela M Cordero Garcia
(74) *Attorney, Agent, or Firm* — Ade & Company Inc.; Michael R. Williams

(57) ABSTRACT

Several species of bacteria capable of invasive infections, such as *S. pyogenes, S. equi* and *P. multocida*, contain hyaluronic acid (HA) in their capsules. Bacterial species such as *Staphylococcus aureus* and related Staphylococci have capsules that contain acidic polysaccharides. Bacterial capsule or bacterial surface binding peptides were synthesized and tested in a culture model of invasive bacterial infections, specifically translocation through polarized keratinocyte cultures. The peptides reduced the translocation of a variety of bacterial species, with a concomitant increase in bacterial internalization by the keratinocytes. In vivo, subcutaneous inoculation of encapsulated GAS treated with peptides delayed bacterial dissemination. In a mouse surgical wound model infected with *S. aureus*, treatment with peptides reduced the numbers of bacteria and inflammation at the wound site.

10 Claims, 6 Drawing Sheets

HYALURONIC ACID BINDING PEPTIDES ENHANCE HOST DEFENSE AGAINST PATHOGENIC BACTERIA

PRIOR APPLICATION INFORMATION

This application claims the benefit of U.S. Provisional Patent Application 60/688,343, filed Jun. 8, 2005, now abandoned and U.S. provisional Patent Application 60/733807, filed Nov. 7, 2005, now abandoned.

FIELD OF THE INVENTION

The invention relates to the field of peptides that bind to hyaluronic acid and to methods for inhibiting bacterial infections using such peptides.

BACKGROUND OF THE INVENTION

Bacterial infections are currently treated by administration of antibiotics to the infected patient. Antibiotics slow bacterial growth or kill bacteria by various mechanisms including disruption of cell membranes, inhibition of bacterial cell wall synthesis, inhibition of bacterial nucleic acid synthesis, inhibition of bacterial protein synthesis and inhibition of enzymes necessary for bacterial metabolism. In general, antibiotics help decrease the level of infection to a certain threshold, allowing the host's immune system to adjust and help clear the infection. There are drawbacks to using antibiotics. Younger and older patients may be more vulnerable to the toxicity or side effects associated with antibiotics. It is also possible for patients to have or develop allergies to antibiotics. Some antibiotics are also toxic to the patient's helpful, natural flora, which results in upset stomach, diarrhea, etc., which may leave the patient susceptible to new or secondary infections that develop while treating the primary infection. The over-prescription of antibiotics has resulted in many strains of bacteria developing resistance to antibiotics.

Penicillin was the first antibiotic to be identified and used successfully to treat infections in humans. Penicillin is rarely used to treat infections with certain types of bacteria due to widespread resistance of the bacteria to penicillin. New antibiotics have been developed as bacteria become resistant to the current antibiotic being used. Methicillin is an effective antibiotic to treat infections with *E. faecium* and *S. aureus*. Methicillin resistance is widespread and most methicillin-resistant strains are also resistant to multiple antibiotics. The term MRSA refers to Methicillin resistant *Staphylococcus aureus*. Typically, infections with resistant strains of bacteria are first detected in hospital settings and then lead to non-hospital or community-acquired infections. Vancomycin is the antibiotic of last resort to treat infections by methicillin-resistant bacterial strains, and the only antibiotic uniformly effective against MRSA and other methicillin-resistant microbes. However, infections with vancomycin resistant strains of enterococci and *S. aureus* have been detected in hospitals and are increasing in frequency in community-acquired infections. There is a need to develop a new treatment modality to treat bacterial infections.

Many different types of organisms produce cationic antimicrobial peptides, typically 20-40 amino acids in length, for defense against infection. Most are capable of rapidly killing a wide range of microbial cells. The initial interactions of cationic peptides with Gram-negative bacteria are thought to involve binding to surface lipopolysaccharide and consequently distort the outer membrane bilayer. This allows access to the cytoplasmic membrane where peptide channel formation has been proposed to occur. It is increasingly disputed as to whether peptide channel formation leads to dissolution of the proton motive force and leakage of essential molecules or whether it is an intermediate step in the uptake of peptide into the cytoplasm, where it inhibits an essential function by e.g. binding to polyanionic DNA. However, severe life threatening infections still occur, indicating that virulent bacteria have developed methods to circumvent the innate cationic antimicrobial peptides.

Exemplary antimicrobial peptides include, but are not limited to, cecropins, normally made by lepidoptera (Steiner et al., Nature 292:246, 1981) and diptera (Merrifield et al., Ciba Found. Symp. 186:5, 1994), by porcine intestine (Lee et al., Proc. Nat'l Acad. Sci. USA 86:9159, 1989), by blood cells of a marine protochordate (Zhao et al., FEBS Lett. 412:144, 1997); synthetic analogs of cecropin A, melittin, and cecropin-melittin chimeric peptides (Wade et al., Int. J. Pept. Protein Res. 40:429, 1992); cecropin B analogs (Jaynes et al., Plant Sci. 89:43, 1993); chimeric cecropin A/B hybrids (During, Mol. Breed. 2:297, 1996); magainins (Zasloff, Proc. Nat'l Acad. Sci. USA 84:5449, 1987); cathelin-associated antimicrobial peptides from leukocytes of humans, cattle, pigs, mice, rabbits, and sheep (Zanetti et al., FEBS Lett. 374:1, 1995); vertebrate defensins, such as human neutrophil defensins [HNP 1-4]; paneth cell defensins of mouse and human small intestine (Oulette and Selsted, FASEB J. 10:1280, 1996; Porter et al., Infect. Immun. 65:2396, 1997); vertebrate .beta.-defensins, such as HBD-1 of human epithelial cells (Zhao et al., FEBS Lett. 368:331, 1995); HBD-2 of inflamed human skin (Harder et al., Nature 387:861, 1997); bovine beta.-defensins (Russell et al., Inject. Immun. 64:1565, 1996); plant defensins, such as Rs-AFP1 of radish seeds (Fehlbaum et al., J. Biol. Chem. 269.33159, 1994); alpha.- and beta.-thionins (Stuart et al., Cereal Chem. 19:288, 1942; Bohlmann and Apel, Annu. Rev. Physiol. Plant Mol. Biol. 42:227, 1991); .gamma.-thionins (Broekaert et al., Plant Physiol. 108:1353, 1995); the anti-fungal drosomycin (Fehlbaum et al., J. Biol. Chem. 269:33159, 1994); apidaecins, produced by honey bee, bumble bee, cicada killer, hornet, yellow jacket, and wasp (Casteels et al., J. Biol. Chem. 269: 26107, 1994; Levashina et al., Eur. J. Biochem. 233:694, 1995); cathelicidins, such as indolicidin and derivatives or analogues thereof from bovine neutrophils (Falla et al., J. Biol. Chem. 277:19298, 1996); bacteriocins, such as nisin (Delves-Broughton et al., Antonie van Leeuwenhoek J. Microbiol. 69:193, 1996); and the protegrins and tachyplesins, which have antifungal, antibacterial, and antiviral activities (Tamamura et al, Biochim. Biophys. Acta 1163:209, 1993; Aumelas et al., Eur. J. Biochem. 237:575, 1996; Iwanga et al., Ciba Found. Symp. 186:160, 1994). An alternative to treating bacterial infections with antibiotics is to block or inhibit bacterial virulence factors that promote and potentiate infections. However, bacteria produce a wide variety of virulence factors that have many different effects on a host. As such, blocking or inhibiting only one virulence factor is likely to have only a marginal effect on an infection. For example, *S. aureus* expresses many virulence factors that are grouped as: (1) surface proteins that promote colonization of host tissues; (2) invasins that promote bacterial spread in tissues (e.g. leukocidin, kinases, hyaluronidase); (3) surface factors that inhibit phagocytic engulfment (e.g. capsule, Protein A); (4) biochemical properties that enhance bacterial survival within phagocytes (e.g. carotenoids, catalase production); (5) immunological disguises (e.g. Protein A, coagulase, clotting factor); (6) membrane-damaging toxins that lyse eukaryotic cell membranes (e.g. hemolysins, leukotoxin, leukocidin; (7) exotoxins or enterotoxins that damage host tissues or otherwise provoke symptoms of disease (e.g. SEA-G, TSST, ET) and (8) inherent and acquired resistance to antimicrobial agents. Such staphylococci virulence factors promote the invasion of host tissues and avoidance of host defenses by methods that include the killing of host immune cells and the generation of superantigens that non-specifically overstimulate the host immune system thereby inhibiting a coordinated response against the pathogens by the immune system. For the majority of diseases caused by *S. aureus*, pathogenesis is multifactorial, so it is difficult to determine precisely the role of any given factor or combination of factors.

It is not clear which of the virulence factors are important for which bacteria, and it is not clear if a virulence factor that has been identified as important in one bacterial species is present and also important in another species.

SUMMARY OF THE INVENTION

The inventors have discovered that treatment of an animal having a bacterial infection with a peptide having basic amino acid residues and capable of binding to hyaluronic acid which may be present on the bacterial capsule, membrane or in the host tissue results in inhibition of the infection in the animal. According to the invention, there is provided the use of a hyaluronic acid binding peptide to inhibit a bacterial infection in an animal.

According to the invention, there is provided the use of a peptide containing a motif formula $B_1$-$X_7$-$B_2$, to inhibit a bacterial infection in an animal.

In one embodiment, the present invention provides a method of treating a bacterial infection by administering an effective amount of a peptide that binds hyaluronic acid comprising a sequence of the formula I:

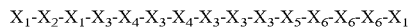

wherein
each $X_1$ is independently selected from an hydroxy amino acid residue;
each $X_2$ is independently selected from a sulfur-containing amino acid residue;
each $X_3$ is independently selected from a basic amino acid residue;
each $X_4$ is independently selected from an imino or aromatic amino acid residue;
each $X_5$ is independently selected from a dicarboxylic acid amino acid residue; and
each $X_6$ is independently selected from an aliphatic amino acid residue;

In a preferred embodiment, the present invention provides a hyaluronic acid binding peptide comprising a sequence of the formula I:

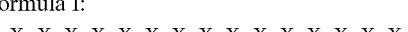

wherein
each $X_1$ is independently selected from threonine or serine;
each $X_2$ is independently selected from methionine or cysteine;
each $X_3$ is independently selected from arginine, lysine or histidine;
each $X_4$ is independently selected from proline, phenylalanine or tryptophan;
each $X_5$ is independently selected from asparagine or glutamine; and
each $X_6$ is independently selected from leucine, isoleucine, valine or alanine, and fragments, analogs or derivatives of the peptide which can bind HA.

A preferred peptide of Formula I is TMTRPHFHKRQLVLS (SEQ. ID. NO.:1).

In another embodiment, the present invention provides a hyaluronic acid binding peptide comprising a sequence of the Formula II:
(b) a sequence of the formula II:

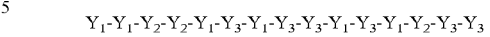

wherein
each $Y_1$ is independently selected from an hydroxy amino acid residue;
each $Y_2$ is independently selected from a sulfur-containing amino acid residue; and
each $Y_3$ is independently selected from a basic amino acid residue.

In a preferred embodiment, the present invention provides a hyaluronic acid binding peptide comprising a sequence of the Formula II:

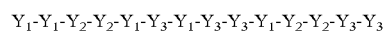

wherein
each $Y_1$ is independently selected from serine or threonine;
each $Y_2$ is independently selected from methionine or cysteine; and
each $Y_3$ is independently selected from arginine, lysine or histidine, and fragments, analogs or derivatives of the peptide which bind HA.

A preferred peptide of the Formula II is STMMSRSHKTRSCHH (SEQ. ID. NO.:2).

In another embodiment, the present invention provides a hyaluronic acid binding peptide comprising a sequence of the Formula III:

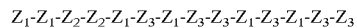

wherein
each $Z_1$ is independently selected from an hydroxy amino acid residue;
each $Z_2$ is independently selected from a sulfur-containing amino acid residue; and
each $Z_3$ is independently selected from a basic amino acid residue, and fragments, analogs or derivatives of the peptide which bind HA.

In a preferred embodiment, the present invention provides a hyaluronic acid binding peptide comprising a sequence of the Formula III:

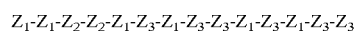

wherein
each $Z_1$ is independently selected from serine or threonine;
each $Z_2$ is independently selected from methionine or cysteine; and
each $Z_3$ is independently selected from arginine, lysine or histidine, and fragments, analogs or derivatives of the peptide which bind the cell surface and/or capsule of the bacteria.

A preferred peptide of the Formula III is STMMSRSHKTRSHH (SEQ. ID. NO.:3). A peptide of the Formula III may optionally contain a valine residue at the C-terminal and have the following sequence: STMMSRSHKTRSHHV (SEQ. ID. NO.:4).

DETAILED DESCRIPTION OF THE PREFERRED EMBODIMENTS

Figure 1:
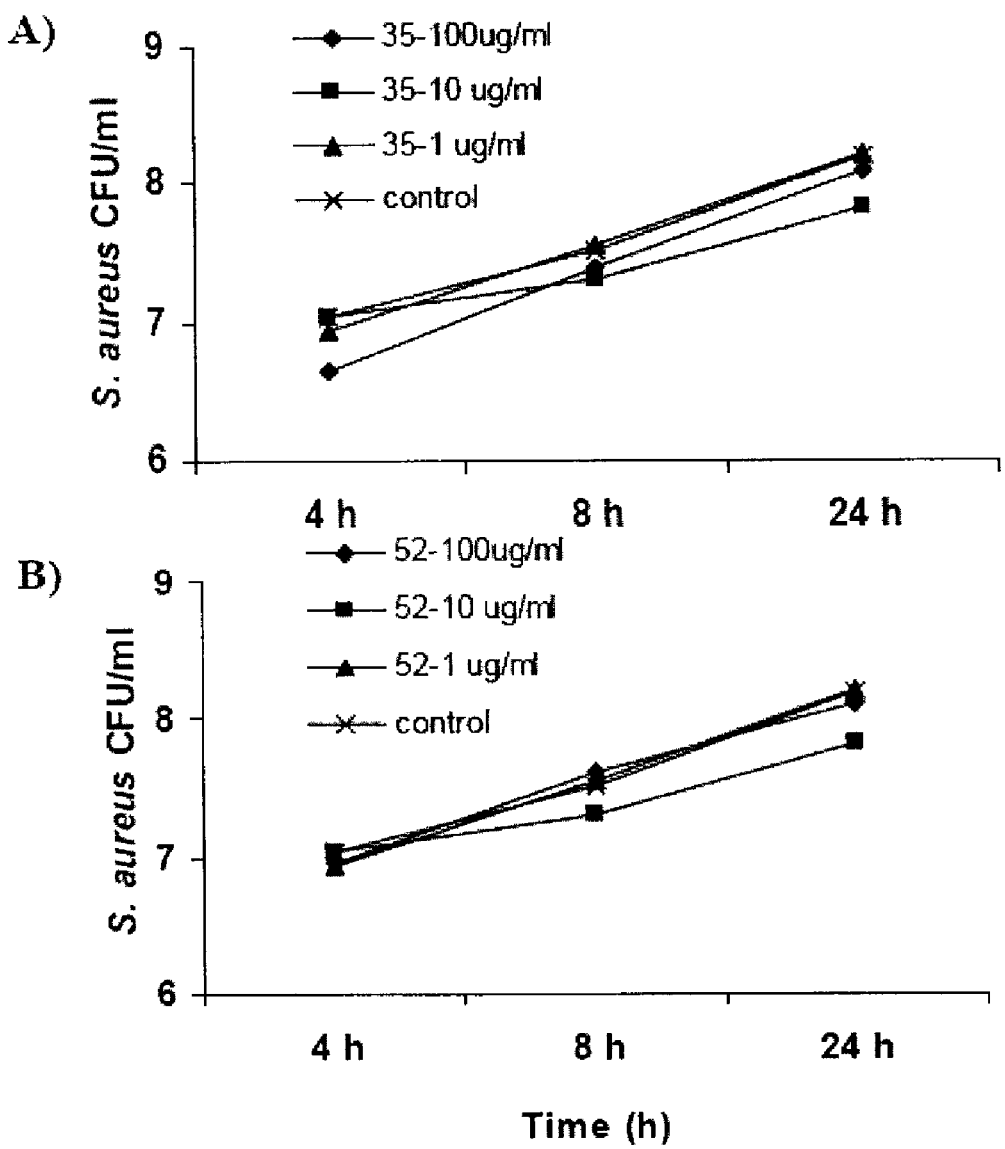
FIG. 1: Effect of hyaluronic acid binding peptides on staphylococcal growth.

The term "amino acid" as used herein includes the twenty alpha-amino acids found in mammalian proteins, including both the L-isomeric and D-isomeric forms. The term also includes alternate amino acid residues, such as hydroxyproline, α-aminoisobutyric acid, sarcosine, citrulline, cysteic acid, t-butylglycine, t-butylalanine, phenylglycine, cyclohexylalanine, β-alanine, 4-aminobutyric acid, and so forth, which can also be included in the peptide sequence in a completely analogous way. The D forms of the encoded amino acids and of alternate amino acids can, of course, also be employed. The manner of determining relative rate constants, of conducting syntheses, and of conducting selection and analysis is entirely analogous to that described below for the naturally-occurring amino acids. Accordingly, the results in terms of the number of rate constants required, the number of representative peptides in the mixture, etc., are also directly applicable to peptides that include as one, or more, or all residues, these nonencoded amino acids.

The following standard one letter and three letter abbreviations for the amino acid residues may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenylalanine; P, Pro—Proline; S, Ser—Serine; T, Thr—Threonine; W, Trp—Tryptophan; Y, Tyr—Tyrosine; and V, Val—Valine;

Hyaluronic Acid Binding Peptides

The present inventor has demonstrated that treatment of animals having a bacterial infection with peptides that bind hyaluronic acid inhibit bacterial infections The therapeutic peptides of the instant invention may be 9 to 100 amino acid residues in length, and preferably 15 to 50 amino acids, and preferably 15 to 40 amino acid residues in length.

The therapeutic peptide may contain at least one repetition of the amino acid residue sequence $B_1$-$X_7$-$B_2$ where B is any basic amino acid residue and $X_7$ are any 7 non-acidic amino acid residues. The binding of the peptide to hyaluronic acid may be enhanced by the addition of basic animo acid residues between B1 and B2 or flanking either end of motif (non-conservative substitutions). Other hyaluronic acid binding motifs or domains may also be present in an HA-binding peptide. For instance, proteins such as CD44 and TSG-6 and proteoglycans such as link protein, aggrecan, brevican, neurocan and versican possess conserved HA-binding regions of approximately 100 amino acids, known as link domains. Peptides isolated by phage display and containing a simple R—R repeat and no other known HA binding motif have also been shown to bind specifically to HA, albeit with somewhat lower affinity than peptides containing the B-X7-B motif. R—R motifs have been identified in link protein, CD44, aggrecan and versican, as well as in RHAMM, cdc37, P-32, SPACR and SPACRCAN, but the contribution of this motif to HA binding by these molecules is uncertain (Amemiya et al, Biochimica et Biophysica Acta 1724 (2005) 94-99).

Another peptide isolated by phage display, HABP52, has been shown to bind to hyaluronic acid (HA) with high affinity and to inhibit leukocyte adhesion to HA as described in U.S. Pat. No. 6,653,285. These peptides lacks similarity to the HA binding motifs discussed above. HABP52 inhibits contact hypersensitivity responses in mice by blocking skin-directed trafficking of inflammatory leukocytes. The HABP52 family of peptides includes peptides with an amino acid sequence selected from the group consisting of: i) Gly-Ala-His-Trp-Gln-Phe-Asn-Ala-Leu-Thr-Val-Arg or a conservative amino acid substitution thereof at a residue position other than 4, 5, 6, 9, 10 or 11; ii) Gly-Ala-Ala-Trp-Gln-Phe-Asn-Ala-Leu-Thr-Val-Arg or a conservative amino acid substitution thereof at a residue position other than 4, 5, 6, 9, 10 or 11; iii) Gly-Ala-His-Trp-Gln-Phe-Ala-Ala-Leu-Thr-Val-Arg or a conservative amino acid substitution thereof at a residue position other than 4, 5, 6, 9, 10 or 11; and iv) Gly-Ala-His-Trp-Gln-Phe-Asn-Ala-Leu-Thr-Val-Ala or a conservative amino acid substitution thereof at a residue position other than 4, 5, 6, 9, 10 or 11.

In one embodiment, the present invention provides method of treating a bacterial infection by administering an effective amount of a peptide that binds hyaluronic acid comprising a sequence of the formula I:

$$X_1\text{-}X_2\text{-}X_1\text{-}X_3\text{-}X_4\text{-}X_3\text{-}X_4\text{-}X_3\text{-}X_3\text{-}X_3\text{-}X_5\text{-}X_6\text{-}X_6\text{-}X_6\text{-}X_1$$

wherein
each $X_1$ is independently selected from an hydroxy amino acid residue;
each $X_2$ is independently selected from a sulfur-containing amino acid residue;
each $X_3$ is independently selected from a basic amino acid residue;
each $X_4$ is independently selected from an imino or aromatic amino acid residue;
each $X_5$ is independently selected from a dicarboxylic acid amino acid residue; and
each $X_6$ is independently selected from an aliphatic amino acid residue;

In a preferred embodiment, the present invention provides a hyaluronic acid binding peptide comprising a sequence of the formula I:

$$X_1\text{-}X_2\text{-}X_1\text{-}X_3\text{-}X_4\text{-}X_3\text{-}X_4\text{-}X_3\text{-}X_3\text{-}X_3\text{-}X_5\text{-}X_6\text{-}X_6\text{-}X_6\text{-}X_1$$

wherein
each $X_1$ is independently selected from threonine or serine;
each $X_2$ is independently selected from methionine or cysteine;
each $X_3$ is independently selected from arginine, lysine or histidine;
each $X_4$ is independently selected from proline, phenylalanine or tryptophan;
each $X_5$ is independently selected from asparagine or glutamine; and
each $X_6$ is independently selected from leucine, isoleucine, valine or alanine, and fragments, analogs or derivatives of the peptide which can bind HA.

A preferred peptide of Formula I is TMTRPHFHKRQLVLS (SEQ. ID. NO.:1).

In another embodiment, the present invention provides a hyaluronic acid binding peptide comprising a sequence of the Formula II:
(b) a sequence of the formula II:

$$Y_1\text{-}Y_1\text{-}Y_2\text{-}Y_2\text{-}Y_1\text{-}Y_3\text{-}Y_1\text{-}Y_3\text{-}Y_3\text{-}Y_1\text{-}Y_2\text{-}Y_3\text{-}Y_3$$

wherein each $Y_1$ is independently selected from an hydroxy amino acid residue;
each $Y_2$ is independently selected from a sulfur-containing amino acid residue; and
each $Y_3$ is independently selected from a basic amino acid residue.

In a preferred embodiment, the present invention provides a hyaluronic acid binding peptide comprising a sequence of the Formula II:

$$Y_1\text{-}Y_1\text{-}Y_2\text{-}Y_2\text{-}Y_1\text{-}Y_3\text{-}Y_1\text{-}Y_3\text{-}Y_3\text{-}Y_1\text{-}Y_2\text{-}Y_3\text{-}Y_3$$

wherein
each $Y_1$ is independently selected from serine or threonine;
each $Y_2$ is independently selected from methionine or cysteine; and
each $Y_3$ is independently selected from arginine, lysine or histidine, and fragments, analogs or derivatives of the peptide which bind HA.

A preferred peptide of the Formula II is STMMSRSHKTRSCHH (SEQ. ID. NO.:2).

In another embodiment, the present invention provides a hyaluronic acid binding peptide comprising a sequence of the Formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein
each $Z_1$ is independently selected from an hydroxy amino acid residue;
each $Z_2$ is independently selected from a sulfur-containing amino acid residue; and
each $Z_3$ is independently selected from a basic amino acid residue, and fragments, analogs or derivatives of the peptide which bind hyaluronic acid.

In a preferred embodiment, the present invention provides a hyaluronic acid binding peptide comprising a sequence of the Formula III:

$$Z_1\text{-}Z_1\text{-}Z_2\text{-}Z_2\text{-}Z_1\text{-}Z_3\text{-}Z_1\text{-}Z_3\text{-}Z_3\text{-}Z_1\text{-}Z_3\text{-}Z_1\text{-}Z_3\text{-}Z_3$$

wherein
each $Z_1$ is independently selected from serine or threonine;
each $Z_2$ is independently selected from methionine or cysteine; and
each $Z_3$ is independently selected from arginine, lysine or histidine, and fragments, analogs or derivatives of the peptide which bind hyaluronic acid.

A preferred peptide of the Formula III is STMMSRSHKTRSHH (SEQ. ID. NO.:3). A peptide of the Formula III may optionally contain a valine residue at the C-terminal and have the following sequence: STMMSRSHKTRSHHV (SEQ. ID. NO.:4).

Evaluation of Hyaluronic Acid Binding Peptides

The inventors demonstrate that the HABP's are not necessarily bactericidal or have lytic activity, and thus appear to differ in the mode of action of known cationic antimicrobial peptides. Hyaluronic acid, also known as hyaluronan, is a polysaccharide found both in the capsules of some pathogenic bacteria, such as group A *Streptococcus* (GAS), and in the tissues of all vertebrate animals, where it is a major component of the extracellular matrix. In tissue, hyaluronic acid plays both structural and functional roles. For instance, hyaluronic acid is a major component of skin (epidermis), where it is a space-filling molecule and organizer of the extracellular matrix. In addition to this structural role, however, hyaluronic acid also interacts with cell-surface receptors such as CD44 and RHAMM. It is thought that the interaction of hyaluronic acid with CD44 generates a survival signal for keratinocytes (skin cells), and is also responsible for stimulating keratinocytes to participate in wound healing. Moreover, cells of the immune system, such as lymphocytes and Langerhans cells traverse the epidermis using hyaluronic acid-rich extracellular spaces, and this locomotion is dependent upon low-affinity binding of their CD44 receptors to hyaluronic acid.

Hyaluronic acid is also a virulence-enhancing component of the bacterial capsule of Group A *Streptococcus* (GAS), where it plays several roles. The presence of hyaluronic acid in the capsule mediates adherence of GAS to vulnerable host cells displaying the hyaluronic acid cell-surface receptor, facilitating the processes of infection and colonization. The hyaluronic acid-containing capsule also helps GAS evade phagocytosis and epithelial ingestions, by virtue of presenting a surface that is very similar to the surrounding extracellular matrix. This protection allows hyaluronic acid-bearing pathogens to proliferate in the extracellular space and ultimately penetrate deeply into tissue and the bloodstream. Hyaluronic acid bacterial capsules have also been implicated in causing cellular changes via CD44 binding and signaling leading to loss of intercellular tight junctions and subsequent translocation of bacteria between host cells and on to underlying tissue.

The destruction or depolymerization of extracellular hyaluronic acid-based structures by hyaluronidases secreted by pathogens such as streptococci, staphylococci and clostridia is also implicated in increasing the spreading or invasiveness of these bacteria.

Hyaluronic acid binding peptides (HABPs) may modulate the progression of bacterial infection by several distinct mechanisms. The inventors present data that HABP's bind both to HA and to bacteria with HA in the capsules, and that HABP's enhance the phagocytosis of the bacteria by both neutrophils and keratinocytes. Binding of HABPs to hyaluronic acid-containing bacterial capsules may interfere with the ability of the capsule to hide the pathogen from the immune system, allowing for greater recognition and phagocytosis. Binding of HABPs to these capsules may also reduce the ability of the pathogen to adhere to and colonize susceptible tissues or cell types via hyaluronic acid-mediated mechanisms. The inventors also demonstrate that HABP's slow translocation of GAS cells through a polarized keratinocyte layer. Binding of HABPs to capsule may also disrupt the ability of the surface HA to trigger signaling events via CD44 or other hyaluronic acid receptors that lead to loss of intercellular junctions or other pro-infection events.

The inventors demonstrate that HABP's slow the spread of pathogenic GAS in an animal model and results in less inflammation at the site of a Staphylococcal infection. Binding of HABPs to extracellular hyaluronic acid may interfere with the ability of pathogen-secreted hyaluronidases to depolymerize the extracellular matrix, thus slowing the spread of the pathogen. Binding of HABPs to extracellular hyaluronic acid may also interfere with the ability of cells of the immune system to mobilize and move within the extracellular space, thereby reducing inflammation, particularly the damaging inflammation caused by pathogens that can mediate tissue damage and promote further infection.

An important aspect of the peptides of the instant invention is the ability to bind to hyaluronic acid-containing bacterial capsules, and/or prevent or reduce infection by pathogenic bacteria. Any strain of staphylococcyl or streptococcyl bacteria can be used to screen peptides of the present invention. Strains for testing may be obtained from sources such as the ATCC, including *S. pyogenes* Su (ATCC 21060), *S. pyogenes* Sv (ATCC 21059), *S. pyogenes* T-12 (ATCC 12353), *S. pyogenes* C-203 (ATCC 12384), *S. pyogenes* (ATCC 19615), *S.*

*pyogenes* (ATCC 12344) and *S. pyogenes* (ATCC 14289), *Pasteurella multocida, Streptococcus equi. Streptococcus pneumoniae* (ATCC 33400), *S. pnemoniae* (ATCC 6303), *S. pneumoniae* (ATCC 35088) and *S. pneumoniae* (ATCC 6314). *Staphylococcus aureus* (ATCC 12598), *S. aureus* (ATCC 33591), *S. aureus* (ATCC 25923), *Staphylococcus epidermidis* (ATCC 12228), and *Enterococcus*. Many methods are known in the art to evaluate the binding of peptides to bacterial cell surface and/or capsule. In one method, the bacteria are immobilized or fixed to a surface such as a multiwell plate or glass slide. The peptide is labeled with a fluorescent tag, mixed in the wells, and the binding determined by measuring the retained fluorescence in the well after washing. A binding peptide will have at least a 10 fold greater fluorescence compared to a control peptide such as SCRM described herein. Peptides can be screened for binding to the capsule of, for example, *S. pyogenes, S. pneumoniae, Pasteurella multocida, Streptococcus equi* and *Staphylococcus aureus*.

Peptides of the instant invention that have multiple hyaluronic acid binding sites, such as peptide 35 described herein, may result in the bacteria clumping when mixed with peptide, demonstrating capsule binding. It is predicted that the clumping is the result of the peptide cross-linking the bacteria. Such bacterial clumping is observed when peptide 35 is added to cultures of *S. aureus* and *S. pyogenes*.

Efficacy testing can be performed using standard procedures. For example, primary efficacy evaluation may be done using any standard in vivo bacterial infection model. Treatment is initiated, varying either or both time(s) of treatment and dose of peptide. A positive result is indicated by significant increase in protection from the infection by the peptide, compared to a negative control. The examples of infection models provided are not limiting. As understood by those skilled in the art, other models can be utilized as appropriate for a specific infecting microbe. In particular, cell-based infection models may be used in some circumstances instead of animal models.

Evaluation of Infection Modulating Activity

Activity of peptides of the instant invention can be assayed by using in vitro models or animal models to evaluate infection modulating activity. These assays are presently described in the literature and are familiar to those skilled in the art. These include but are not limited to assays for monitoring inflammation, extent of microbial infection and the phagocytosis of bacteria by mammalian cells involved in immunity such as neutrophils, eosinophils, macrophage and keratinocytes. Compounds of the present invention can be screened for infection modulating activity by measuring their ability to inhibit bacterial translocation through a polarized keratinocyte epithelium.

The term "binding peptide", "peptides" or "HABP" as used herein means a peptide that can bind to hyaluronic acid and is of the formulae as defined above. The peptides of the instant invention were initially designed to bind to hyaluronic acid (HA). However, the peptides may also bind to other molecules or targets, as evidenced by the ability of the peptides to bind and inhibit infections by bacterial species such as *Staphylococcus aureus*, which is not known to contain hyaluronic acid in the capsule, or species that do not have a capsule. Bacterial cell surface targets for HABP binding may include other glycosaminoglycans, acidic polysaccharide molecules, glycolipids, peptidoglycan, lipopolysaccharide, and proteins. The term includes fragments, analogs and derivatives of the peptides, which maintain the ability to bind hyaluronic acid or other targets. Collectively, the hyluronic acid binding peptides defined herein are referred to as the peptides of the invention. The therapeutic peptides may be composed of amino acid residues in the levorotatory L-stereoisomer form, which corresponds to how amino acids occur in nature, or the dextrorotatory or D-stereoisomer, or the peptides may be composed of a mixture of L and D stereoisomers of amino acid residues.

The term "analog" includes any peptide having an amino acid residue sequence substantially identical to the sequence of the bacterial capsule binding peptides shown in Formula I, II, or III shown herein in which one or more residues have been conservatively substituted with a functionally similar residue and which displays the ability to mimic a hyaluronic acid binding peptide. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically-derivatized residue in place of a non-derivatized residue provided that such polypeptide displays the requisite bacterial binding activity. Substantially identical shall mean a peptide that retains at least 75% homology and retains the ability to bind hyaluronic acid.

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as derivatives are those peptides that contain one or more amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Hyaluronic acid binding peptides of the present invention also include any peptide having one or more additions and/or deletions of residues relative to the sequence of a polypeptide whose sequence is shown herein, so long as the requisite binding activity is substantially maintained.

The term "fragment" refers to any subject peptide having an amino acid residue sequence shorter than that of a peptide whose amino acid residue sequence is shown herein.

The invention includes cyclic derivatives of the hyaluronic acid binding peptides of the invention. Cyclization allows the peptide to assume a more favourable conformation. Cyclization of the peptides may be achieved using techniques known in the art. In particular, disulphide bonds may be formed between two appropriately spaced components having free sulfhydryl groups. The bonds may be formed between side chains of amino acids, non-amino acid components or a combination of the two.

The peptides of the invention may be prepared as N-terminal or C-terminal fusion proteins. The fusion proteins may be prepared by fusing, through recombinant techniques or by chemical crosslinking, the N-terminal or C-terminal of the peptide, and the sequence of a selected protein or selectable marker with a desired biological function. The resultant fusion proteins contain the peptide fused to the selected protein or marker protein as described herein. Examples of proteins that may be used to prepare fusion proteins include immunoglobulins, glutathione-S-transferase, hemagglutinin, and truncated myc.

The peptides of the invention may be labeled using conventional methods with various enzymes, fluorescent materials, luminescent materials and radioactive material. Suitable enzymes, fluorescent materials, luminescent materials, and radioactive material are well known to the skilled artisan.

Preparation of the Peptides

The peptides of the invention may be prepared by chemical synthesis using techniques well known in the chemistry of proteins such as solid phase synthesis (Merrifield, J. Am. Chem. Assoc. 85:2149-2154 (1964)) or synthesis in homogenous solution (Houbenweyl, Methods of Organic Chemistry, ed. E. Wansch, Vol. 15 I and II, Thieme, Stuttgart (1987)).

The peptides of the invention may also be produced by recombinant DNA technology. To prepare the peptides of the invention by recombinant DNA techniques, a DNA sequence encoding the bacterial capsule-binding peptide must be prepared and inserted into recombinant expression vectors that can be introduced into host cells to produce a transformant host cell. Suitable host cells include a wide variety of prokaryotic and eukaryotic host cells. For example, the proteins of the invention may be expressed in bacterial cells such as E. coli, insect cells (using baculovirus), yeast cells or mammalian cells. The recombinant expression vectors containing the nucleotide sequences encoding the bacterial capsule-binding peptides may also contain genes which encode a fusion moiety which provides increased expression of the recombinant peptide; increased solubility of the recombinant peptide; and aid in the purification of the target recombinant peptide by acting as a ligand in affinity purification. For example, a proteolytic cleavage site may be added to the target recombinant protein to allow separation of the recombinant protein from the fusion moiety subsequent to purification of the fusion protein.

Pharmaceutical Compositions and Delivery

Peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

The presently described peptides may be formulated with a variety of physiological carrier molecules. The isolated peptides may also be complexed with molecules that enhance their ability to target bacterial cells or sites of infection. Examples of such molecules include, but are not limited to, carbohydrates, polyamines, amino acids, peptides, lipids, and molecules vital to bacterial growth. For example, the peptides may be combined with a lipid, cationic lipid, or anionic lipid. The resulting peptide/lipid emulsion, or liposomal suspension may, inter alia, effectively increase the in vivo half-life of the peptide. Examples of suitable anionic lipids for use with therapeutic peptides include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol. The use of cationic, anionic, and/or neutral lipid compositions or liposomes is generally described in International Publications Nos. WO 90/14074, WO 91/16024, WO 91/17424, and U.S. Pat. No. 4,897,355, herein incorporated by reference. By assembling the glycoaminoglycan-modulating peptides into lipid-associated structures, the peptides may be targeted to specific bacterial cell types by the incorporation of suitable targeting agents (i.e., specific antibodies or receptors) into the peptide/lipid complex.

Pharmaceutical compositions containing the peptides of the invention in admixture with a pharmaceutical carrier can be prepared according to conventional pharmaceutical compounding techniques. The carrier may take a wide variety of forms depending on the form of the preparation desired for administration, e.g., intravenous, oral, topical, aerosol (for topical or pulmonary delivery), suppository, parenteral, ocular, surgical wash, or spinal injection.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated and enteric-coated by standard techniques.

For parenteral application by injection, preparations may comprise an aqueous solution of a water soluble, or solubilized, and pharmaceutically acceptable form of the peptide in an appropriate saline solution. Injectable suspensions may also be prepared using appropriate liquid carriers, suspending agents, agents for adjusting the isotonicity, preserving agents, and the like. Actual methods for preparing parenterally administrable compositions and adjustments necessary for administration to subjects will be known or apparent to those skilled in the art and are described in more detail in, for example, Remington's Pharmaceutical Science, 15th Ed., Mack Publishing Company, Easton, Pa. (1980), which is incorporated herein by reference. The presently-described peptides should be parenterally administered at concentrations below the maximal tolerable dose (MTD) established for the particular peptide to be administered.

For topical administration, the carrier may take a wide variety of forms depending on the preparation, which may be a cream, skin patch, shampoo, dressing, gel, lotion, ointment, ear drops, eye drops, or liquid.

Aerosols can be prepared by dissolving or suspending the isolated protein preparation in a propellant such as ethyl alcohol or in propellant and solvent phases. The pharmaceutical compositions for topical or aerosol form will generally contain from about 0.01% by weight (of the peptide) to about 40% by weight, preferably about 0.02% to about 10% by weight, and more preferably about 0.05% to about 5% by weight depending on the particular form employed.

Suppositories are prepared by mixing the peptide with a lipid vehicle such as theobroma oil, cacao butter, glycerin, gelatin, or polyoxyethylene glycols.

The presently-described isolated peptides and their compositions may be administered to the body by virtually any means used to administer conventional antibiotics. A variety of delivery systems are well known in the art for delivering bioactive compounds to an animal. These systems include, but are not limited to, oral, parenteral, sublingual, bladder wash-out, vaginal, rectal, enteric, suppository, nasal, and inhalation. The term parenteral, as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The specific delivery system used depends on the location of the area to be treated, and it is well within the skill of one in the art to determine the location and to select an appropriate delivery system.

Suitable examples of sustained-release preparations include semipermeable matrices of solid hydrophobic polymers containing the peptide, which matrices are in the form of shaped articles, e.g., films, or microcapsules. Examples of sustained-release matrices include polyesters, hydrogels (e.g., poly(2-hydroxyethyl-methacrylate) as described by Langer et al. (1981) J. Biomed. Mater. Res. 15:167-277 and Langer (1982) Chem. Tech. 12:98-105, or poly(vinyl alcohol)), polylactides (U.S. Pat. No. 3,773,919, EP 58,481), copolymers of L-glutamic acid and gamma ethyl-L-glutamate (Sidman et al. (1983) Biopolymers 22:547-556), non-degradable ethylene-vinyl acetate (Langer et al. (1981) supra) degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

Peptide compositions also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

While polymers such as ethylene-vinyl acetate and lactic acid-glycolic acid enable release of molecules for over 100 days, certain hydrogels release molecules for shorter time periods. When encapsulated molecules remain in the body for a long time, they may denature or aggregate as a result of exposure to moisture at 37° C., resulting in a loss of biological activity and possible changes in immunogenicity. Rational strategies can be devised for stabilization depending on the mechanism involved, e.g., using appropriate additives, and developing specific polymer matrix compositions.

Sustained-release compositions also include liposomally entrapped peptides. Liposomes containing compositions of the invention are prepared by methods known per se: DE 3,218,121; Epstein et al. (1985) Proc. Natl. Acad. Sci. USA 82:3688-3692; Hwang et al. (1980) Proc. Natl. Acad. Sci. USA 77:4030-4034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol % cholesterol, the selected proportion being adjusted for the optimal therapy. A specific example of a suitable sustained-release formulation is in EP 647,449.

An effective amount of composition to be employed therapeutically will depend, for example, upon the therapeutic objectives, the route of administration, and the condition of the patient. Accordingly, it will be necessary for the clinician to titer the dosage and modify the route of administration as required to obtain the optimal therapeutic effect. A typical daily dosage of a molecule used alone might range from about 1 μg/kg to up to 100 mg/kg of patient body weight or more per day, depending on the factors mentioned above, preferably about 10 μg/kg/day to 50 mg/kg/day.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Bacterial Infections

Peptides of the instant invention may be used to treat patients infected with bacteria to which the peptides may or may not bind. The patients may be humans but the peptides may also be used in veterinary applications. The peptides may be used to treat infections with *Staphylococcus aureus*, which causes a variety of suppurative (pus-forming) infections and toxinoses in humans. *S. aureus* causes superficial skin lesions such as impetigo, boils, styes and furunculosis; more serious infections such as pneumonia, mastitis, phlebitis, meningitis, and urinary tract infections; and deep-seated infections, such as cellulitis, osteomyelitis and endocarditis. *S. aureus* is a major cause of hospital-acquired (nosocomial) infection of surgical wounds and infections associated with indwelling medical devices. *S. aureus* causes food poisoning by releasing enterotoxins into food, and toxic shock syndrome by release of superantigens into the blood stream. *Staphylococcus epidermidis* inhabits the skin of healthy humans, but poses a threat to immunocompromised individuals. *S. epidermidis* is also resistant to many antibiotics.

Peptides from the instant invention may also be used to treat infection by Enterococci species such as *E. faecalis*, *E. durans*, and *E. faecium* (formerly *S. faecalis*, *S. durans*, *S. faecium*), and the nonenterococcal streptococci, of which *S. bovis* and *S. equinus* are the most common. Most infections of humans are caused by *E. faecalis*, *E. faecium*, or *S. bovis*. Like the enterococci, *S. bovis* is commonly found in the GI tract. *S. bovis* is an important cause of bacterial endocarditis, particularly when an intestinal neoplasm or other significant lesion is present. *E. faecalis* and *E. faecium* cause endocarditis, UTIs, intra-abdominal infections, cellulitis, and wound infection as well as concurrent bacteremia.

Peptides from the instant invention may also be used to treat infection by streptococci species. Group A streptococci (*S. pyogenes*) are the most virulent species for humans, causing pharyngitis, tonsillitis, wound and skin infections, septicemia, scarlet fever, pneumonia, rheumatic fever, and glomerulonephritis. Necrotizing fasciitis is one of the most deadly Group A Strep infections, due to its rapid progression that attacks the deep layers of tissue (fascia). Invasive streptococci also cause joint or bone infections, destructive wound infections and myositis, meningitis and endocarditis. Group B streptococci, also known as *S. agalactiae*, cause serious infections, particularly neonatal sepsis, postpartum sepsis, endocarditis, and septic arthritis. Viridans streptococci consist of five main species: *S. mutans*, *S. sanguis*, *S. salivarius*,

*S. mitior*, and *S. milleri*; the latter is further subdivided into *S. constellatus, S. intermedius*, and *S. anginosus*. There is still disagreement about their classification and identification. *S. iniae*, a pathogen in fish, is capable of causing outbreaks of cellulitis and invasive infections in patients with skin injuries who handled live or freshly killed aquacultured fish, usually tilapia or trout.

Strangles (*Streptococcus equl*) is an important equine disease that frequently occurs as an outbreak with high morbidity (90%) but low mortality (5%>foals). Strangles is caused by infection with *Streptococcus equi*. Typical signs of infection are increased temperature, loss of appetite, soft cough, purulent nasal discharge and swollen lymph nodes of the face, which may often abscessate and burst.

Peptides from the instant invention may also be used to treat infection by *pasteurella* species. *Pasteurella pneumotropica* is an opportunistic pathogen that is not often associated with clinical diseases. However, when infecting a host, it can generally be recovered from the respiratory tract, the urogenital tract, or conjunctiva from the host: common hosts include mice, rats, hamsters, guinea pigs, rabbits, cats, and other laboratory animals. In the case of humans, many strains from *Pasteurella multocida* subsp. *multocida, Pasteurella multocida* subsp. *septica, Pasteurella canis, Pasteurella stomatis*, and *Pasteurella dogmatis* have been isolated from infected humans. Symptoms of a *Pasteurella* infection vary depending on which body organ is involved and how long the disease is present.

The peptides or analogs or derivatives thereof of the present invention may be used individually, or may be used in combination with one or more different antimicrobial peptides or analogs or derivatives thereof, and one or more conventional antimicrobial agents, as described herein. Thus, synergistic combinations of a hyaluronic acid binding peptide and an antimicrobial agent may permit a reduction in the dosage of one or both agents in order to achieve a similar or improved therapeutic effect. This would allow the use of smaller doses and, therefore, would decrease the potential incidence of toxicity (e.g., from aminoglycosides) and lowering costs of expensive antimicrobials (e.g., vancomycin). Concurrent or sequential administration of a hyaluronic acid binding peptide formulation and an antimicrobial agent composition is expected to provide more effective treatment of infections caused by a variety of microorganisms. In particular, successful treatment or prevention of infectious disease can be achieved by using the hyaluronic acid binding peptides and antimicrobial agents at doses below what is normally a therapeutically effective dose when these agents are used individually. Alternatively, the antibiotic agent and hyaluronic acid binding peptide formulation can be administered using a normally effective therapeutic dose for each agent, but wherein the combination of the two agents provides even more potent effects.

As noted above, the hyaluronic acid binding peptides may be used in a synergistic combination with other known antimicrobial agents. Antibacterial agents include, but are not limited to, penicillins, cephalosporins, carbacephems, cephamycins, carbapenems, monobactams, aminoglycosides, glycopeptides, quinolones, tetracyclines, macrolides, and fluoroquinolones. Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69712-56-7); Cefprozil (CAS Registry No.: 92665-29-7); Lincomycin (CAS Registry No.: 154-21-2); Linezolid (CAS Registry No.: 165800-03-3); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry. No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

EXAMPLES

HABP Peptides: HABP01 is a hyaluronic acid (HA) binding peptide and SCRM is a peptide with an identical amino acid residue composition as HABP01 but with a scrambled sequence. Although HABP01 binds HA it may also bind other molecules. HABP42 has an identical amino acid sequence as HABP01, but is composed of all (d isomer) amino acid residues. HABP33 is based on the HA binding domains of human RHAMM, and is predicted to have one HA binding domain conforming to the motif: basic amino acid-7 amino acids-basic amino acid. BP35 is predicted to have at least two HA binding domains.

| Peptide | Sequence |
|---------|----------|
| HABP01  | STMMSRSHKTRSHHV |
| SCRM    | HKSVSRHTSMRHSTM |
| HABP33  | VSKLRSQLVKRKQN |
| HABP35  | LKQKIKHVVKLKVVVKLRSQLVKRKQN |
| HABP42  | STMMSRSHKTRSHHV (all d isomers) |
| HABP52  | GAHWQFNALTVRGGGS |

HABPs were synthesized with L-amino acids (except HABP42 which is all d-amino acids) and the C-terminus is amidated. The peptides were synthesized by SynPep Corporation (Dublin, Calif.) using standard fMOC chemistry and purified to >95% purity. Each synthetic peptide was analyzed by reverse-phase HPLC to assure the purity, aliquotted 2 mg per vial and lyophilized prior to shipment.

Lyophilized synthetic peptides were resuspended in PBS pH7.4 prior to use in either in vitro or in vivo experiments. Fluorescein conjugation of HABP01 and SCRM was performed using 5,6 carboxyfluorescein, succinimidyl ester (5,6 FAM) (Molecular Probes, Portland, Oreg.) as per manufacturer's instructions and separated on a Sephadex G-25 column (Amersham, Piscataway, N.J.). Purified, high molecular weight rooster comb HA (Sigma-Aldrich, St Louis, Mo.) was used as a positive control for BP binding.

Bacterial strains: GAS strain 950771 is a moderately encapsulated M3 clinical isolate from a child with post-varicella necrotizing fasciitis and sepsis, and an isogenic capsule deficient mutant, 188, derived from 950771. GAS were grown in Todd-Hewitt broth (Difco) to mid-exponential phase OD650 of 0.15 at 37° C. for all experiments. Commercially available trypticase-soy agar medium supplemented with 5% vol/vol sheep blood (BAP)(PML Microbiologicals, British Columbia, Canada) were used for all plate cultures. *S. equi s*(ATCC 53185) and *P. multocida* (ATCC 11039) were purchased from ATCC and cultured as recommended. Briefly, *S. equi* was cultured in Todd-Hewitt broth and *S. uberis* and *P. multocida* were cultured in Brain heart infusion (Difco) to OD 650 of 0.15 at 37° C. Quantitative cultures were performed in parallel with each experiment to verify the multiplicity of infection (MOI) of the inoculum.

Surface Plasmon Resonance Spectroscopy in the Study of Peptide Binding Interactions with Hyaluronic Acid Surface plasmon resonance spectroscopy (SPR) studies were performed on a Biacore T-100 to quantitate the binding of peptides to hyaluronic acid (HA). Biotin-labeled hyaluronic acid (Sigma B1557, hyaluron sodium salt from rooster comb with >97% purity, average approximately 850 kDd, 98% labeled) was immobilized on one of the four flow cells of a streptavidin-coated series S sensor chip SA. One of the remaining three flow cells had no biotin HA immobilized and is used as a control to assess non-specific binding to the chip surface. Peptides were then injected across the surface and the degree of binding interaction is measured in response units (RU).

The average net binding for HABP35 to HA was 399±77 RU or significant binding. The other HA binding peptides also had positive RU values. A 26 amino acid control peptide melittin exhibited a net negative RU response (−503±5 RU) signifying no binding for HA. Specific binding of HABP35 to HA was confirmed by competitive inhibition via addition of unlabeled HA to the HABP35 prior to injection across the immobilized HA surface, which resulted in a −316 RU reading.

Binding of HABP to HA and HA-encapsulated bacteria: To assess whether HABP are able to associate specifically with the GAS capsule, bacteria were cultured to mid-log phase, for maximal HA capsule expression, and incubated with either 10 μg/ml of FITC-conjugated HABP01 or SCRM, with purified HA at 1 mg/ml, as a positive control, or an isogenic mutant strain of GAS deficient in HA capsule, as a negative control. A GAS-specific antibody was used to control for the number of bacteria per well. HABP01 bound specifically to both encapsulated GAS and purified HA, but not to unencapsulated GAS when assessed by fluorometry (Table 1). Control SCRM peptide did not bind to the bacteria or control samples. HABP35 also demonstrated specific binding to encapsulated GAS, and no binding of HABP35 was detected to unencapsulated GAS as determined by confocal microscopy and fluorometry (data not shown).

TABLE 1

Specific binding of HABP001 to hyaluronic acid and to HA encapsulated GAS

| Substrate in well | Relative binding (relative fluorescent units) | | | |
|---|---|---|---|---|
| | BSA/PBS | Anti-GAS | HAPB001 | SCRM |
| HA | 1180 ± 30 | 1340 ± 50 | 9640 ± 360 | 1520 ± 20 |
| Wild Type GAS | 1140 ± 40 | 5760 ± 70 | 11840 ± 230* | 1550 ± 30 |
| Acapsular GAS | 1200 ± 30 | 12860 ± 180 | 1940 ± 70** | 1490 ± 40 |

*P < 0.0004
**P < 0.0001

HABPS do not possess direct microbicidal activity for *S. aureus*. The antimicrobial activity of HABP35 and HABP53 was determined using a modified National Committee for Clinical Laboratory Standards (NCCLS) macrodilution broth method. *S. aureus* PS80 was grown overnight on tryptic soy agar plates containing 5% sheep blood. Colonies were suspended in sterile saline and dilutions made to achieve a final concentration of $5 \times 10^5$ CFU/ml in each tube containing 5 ml of Mueller-Hinton and BP35 or 53. The HABPs were tested at 1, 10, and 100 ug/mL concentrations. Once inoculated, the tubes were incubated in ambient air at 37° C. and bacterial concentration determined at 4, 8, and 24 hours. Modification of testing parameters included the 10 fold dilution of the HABPs and the determination of bacterial counts at 4, 8 and 24 hours rather than the visual determination of growth or inhibition. Quantitative cultures were performed at 4, 8, and 24 h and demonstrated that growth of *S. aureus* was not inhibited by HABP35 or 52 when compared to controls which did not contain the HABPs (FIG. 1).

Determination of Hemolytic Activity of HABP35: Measurement of the hemolytic activity (MHC) of HABP35 was performed to provide an assessment of the toxicity of the peptide in higher eukaryotic cells. A direct comparison of the relative hemolytic activity to an established agent, Melittin, a naturally-occurring strongly hemolytic peptide isolated from bee venom, was included. Determination of hemolytic activity is measured through the release of hemoglobin from human red blood cells as measured spectrophotometrically.

The methodology for determination of hemolysis was according to the twelve-hour protocol described by Chen et al., 2005. Briefly, a dilution series of the peptide was prepared in two-fold dilutions from 512 to 1 µg/mL. Triplicate determinations of each peptide concentration were added to 1% human red blood cells and incubated for 12 hours at 37° C. The negative control for hemolysis consisted of 1% red blood cells with no peptide added. The positive control for hemolysis was 1% red blood cells in 0.15M NH$_4$Cl. Hemoglobin release was measured at an absorbance of 562 nm.

Figure 2:
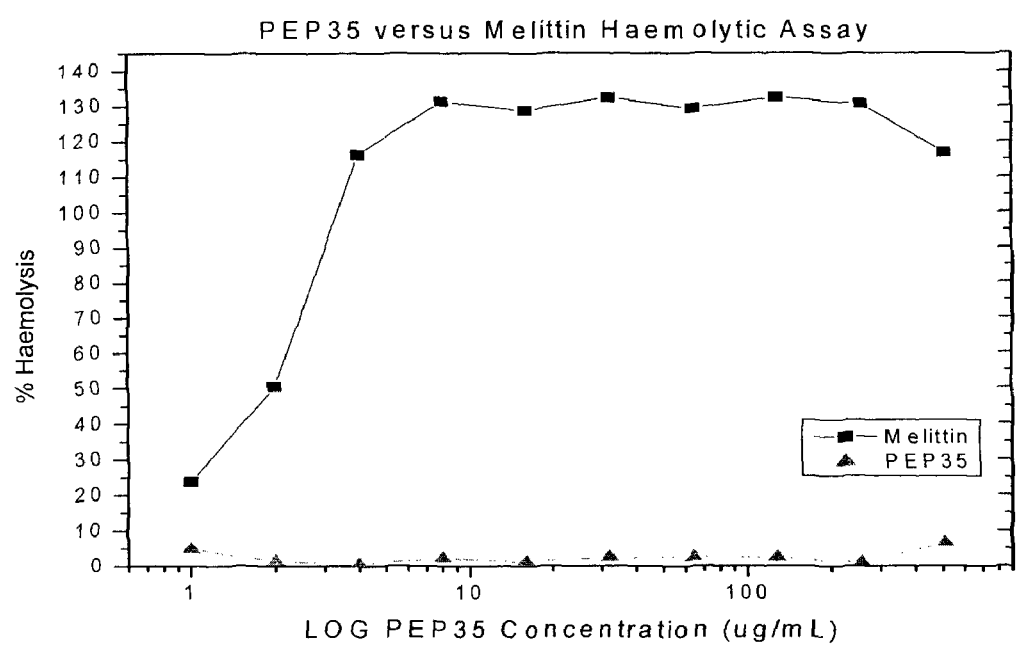
FIG. 2: Hemolytic activity of HABP35.

Percent hemolysis is calculated as the ratio of the optical density (OD) of the peptide relative to the OD of the positive control for hemolysis. The data demonstrates that HABP35 exhibits minor hemolytic activity at the highest concentration (512 µg/mL) tested (FIG. 2). In comparison, Melittin was shown to be more than 500 times more potent as a hemolytic agent with comparable levels of hemolysis observed at a concentration of less than 1 µg/mL. Melittin is considered to be a strongly hemolytic peptide which is comparable to peptide V681 previously determined to have a MHC value of 15.6 ug/mL using the same methodology.

Effect of HABP on bacterial internalization by keratinocytes. Encapsulated GAS are poorly internalized by keratinocytes. Yet in the presence of HABPs, intracellular encapsulated GAS are observed by microscopy. To quantify this internalization, keratinocyte monolayers were infected with HA-encapsulated bacteria in the presence of 100 µg/ml of either HABP01 or SCRM for 4 hours. Penicillin and gentamicin were added at 3 hours to kill extracellular bacteria and cells were harvested. Bacteria treated with HABP01 were internalized approximately 40-fold more efficiently than SCRM-treated or untreated samples, and at similar levels to those obtained with acapsular GAS. Internalization of acapsular GAS was unaffected by either peptide.

HABPs Enhance Killing of GAS by Neutrophils In Vitro

Encapsulated GAS are resistant to killing by neutrophils in opsonophagocytic assays in the absence of antibodies that bind the bacterial surface. HABPs binding to the bacterial surface may facilitate neutrophil cytotoxicity. Opsonophagocytic assays were performed wherein GAS were incubated with 50 µg/ml of SCRM, HABP01 or HABP35 and mixed with human neutrophils in medium containing 10% absorbed human serum. Aliquots (25 µl) for quantitative culture were withdrawn immediately after mixing neutrophil with GAS and after 2 hr incubation at 37° C. The log increase or decrease in CFU's was calculated. After 2 hours of incubation, there was about a 1.5 log increase in CFU's for GAS treated with PBS or SCRM. GAS treated with HABP01 resulted in slightly over 1 log increase in CFU's. However, treatment of GAS with 50 µg/ml of HABP35 resulted in no CFU's detected at 2 hours in the opsonophagocytic assay (p>0.0001). Treating GAS with 5 or 10 µg/ml of HABP35 resulted in >2 log reduction in bacterial numbers at 2 hours (p>0.0001).

The decrease in bacterial counts following treatment with HABP35 is not due to a toxic effect of the peptide on GAS. Quantitative cultures and optical density readings performed at 2, 4, 6, and 24 hours demonstrated GAS cells are capable of growth in cultures with up to 50 µg/ml of HABP35. Thus the dramatic decrease in CFU's observed in the opsonophagocytic assay is likely the result of increased GAS killing by neutrophils in the presence of HABP35.

Assessment of Bacterial Translocation Through Polarized Keratinocyte Cultures.

Cell cultures: For the preparation of in vitro keratinocyte cultures, human primary OKP7 cells were derived from the oropharynx. Keratinocytes were seeded at 5×10$^5$ cells per well onto polycarbonate Transwell membrane supports (12 well plates, 3.0 µm pore size; Costar) or tissue culture treated plastic ware and cultured for 5-10 days at 37° C. with 5% humidified CO$_2$ in cSFM medium with daily medium changes. Once confluent, the calcium concentration of the cSFM was increased to 1.2 mM and cells were cultured for 2 more days, before the integrity of the monolayer was assessed by measuring permeability to sodium fluorescein, and in some experiments, by measuring transepithelial electrical resistance.

Infection procedures: Keratinocyte layer cultures in Transwell inserts were inoculated in the upper chamber with GAS, S. equi, S. uberis, and P. multocida at a multiplicity of infection (MOI) of 1 bacterium per keratinocyte in the presence or absence of HABP01 or SCRM. Infected cultures were incubated at 37° C. with 5% CO$_2$ for the desired time. In translocation experiments, Transwell inserts containing the keratinocytes were moved to new wells containing fresh medium every 2 hours to prevent overgrowth of bacteria that had translocated through the keratinocytes layer to the lower chamber. Bacterial translocation was quantified by culturing medium from the lower chamber at 2-hour intervals.

Figure 3:
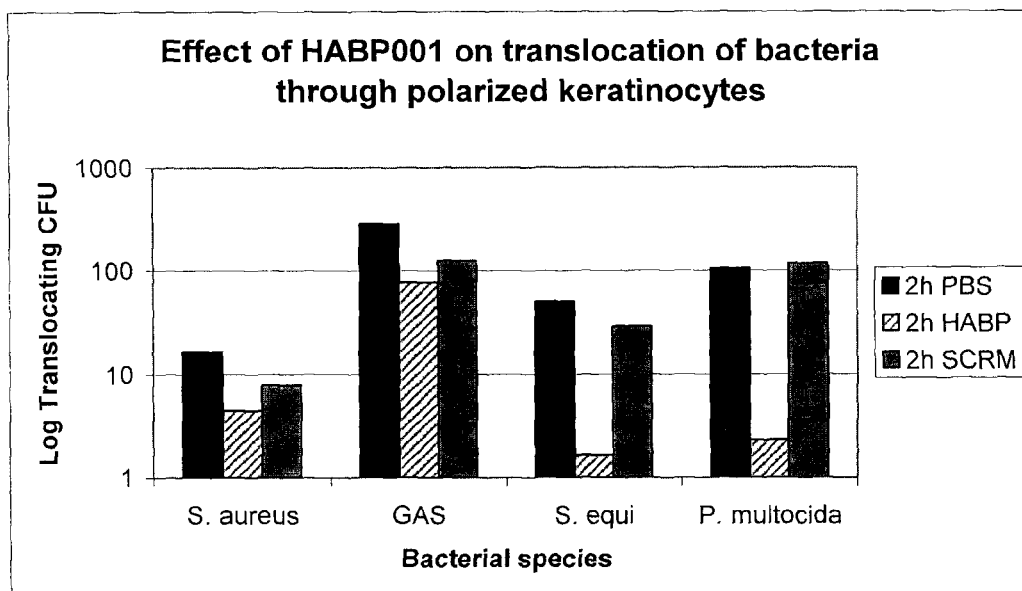
FIG. 3: Translocation of encapsulated Group A *Streptococcus* (GAS), *S. equi, P. multocida* and *Staphylococcus aureus* through polarized keratinocyte cultures

Bacterial translocation studies were performed to assess the impact of HABP01 on bacterial paracellular translocation through polarized keratinocyte cultures. Treatment of either keratinocytes or bacteria with 100 µg/ml HABP01, resulted in a 75-85% reduction in the translocation of GAS across an intact keratinocyte culture, 98% for S. equi, 98% for P. multocida, and 73% for Staphylococcus aureus compared to treatment with PBS or SCRM (FIG. 3).

Incubation of GAS in the presence of HABP33, HABP35 and HABP42, also delayed GAS translocation. At two hours after the addition of GAS to the keratinocytes, approximately 530 CFU of GAS were detected in the lower level in cultures treated with PBS or SCRM peptide. Treatment with either HABP01 or HABP42 resulted in a 75-85% decrease in the numbers of translocating GAS bacteria, and treatment with HABP33 resulted in nearly 90% decrease in translocating GAS. Treatment with HABP35 completely inhibited translocation of GAS across the keratinocyte layer.

Assessing the Role of HABPs in a Mouse Model of Soft Tissue Invasive Infection.

Mouse soft tissue invasive infection model: Female 4-6-week-old CBA/J mice (Jackson Laboratory, Minn.) were inoculated with GAS. Briefly, mice were anesthetized and the hair was shaved off the right flank. Approximately 1.5×10$^5$ cfu of GAS from an early log-phase broth culture were suspended in 50 µl of sterile PBS or HABP and inoculated just under the surface of the skin with a 27-guage needle. The animals were observed twice daily for 3-5 days. Serial tail vein bleeds were performed daily and 50 µl of blood was inoculated on BAP for enumeration of viable bacterial CFU and incubated at 37° C. for 24 hours. Animals surviving the experiment or appearing moribund at any time were euthanized and the spleen removed using aseptic technique. The spleen was homogenized in 1 ml of THB and 100 µl of homogenate plated on BAP. In some experiments animals were euthanized at various time points during infection and tissue sections from the inoculation site were prepared for histopathological examination.

HABP-treated mice repeatedly indicated a 24-hour to 48-hour delay in dissemination of bacteria from the inoculation site compared to controls. Treatment with a single dose of HABP35 completely protected the mice from bacteremia. The delayed dissemination correlated with a reduced mortality 24 hours after infection, but once dissemination occurred, HABP-treated mice died rapidly. Histopathologic analysis of the infection site indicated typical lateral GAS dissemination.

In contrast, HABP-treated mice displayed intact foci of bacteria near the inoculation site with no spreading observed during the first 24 hours.

Confocal microscopy of tissue sections taken from the infection sites of untreated and SCRM peptide-treated GAS infected mice show numerous polymorphonuclear leukocytes (PMNs, including neutrophils, basophils and eosinophils) at the infected site. PMNs were located both within the bacterial mass and in the surrounding tissue and were accompanied by extensive swelling, tissue necrosis, and infarction. In contrast, HABP-treated mice had few PMNs visible in either the tissue surrounding the bacterial foci or within the focus. In sections where breakdown of the bacterial focus is evident, recruited PMNs were visible in contact with disseminating bacteria.

Staphylococcal Infections

Bacterial strains. *S. aureus* strain PS80 (serotype 8) was obtained from the American Type Culture collection (#27700) and is a potent inducer of intraabdominal abscess formation. *S. aureus* COL is a methicillin resistant strain that produces a serotype 5 capsule. Staphylococci were cultivated for 24 h at 37° C. on Columbia agar (Difco Laboratories, Detroit, Mich.) supplemented with 2% NaCl.

Figure 4:
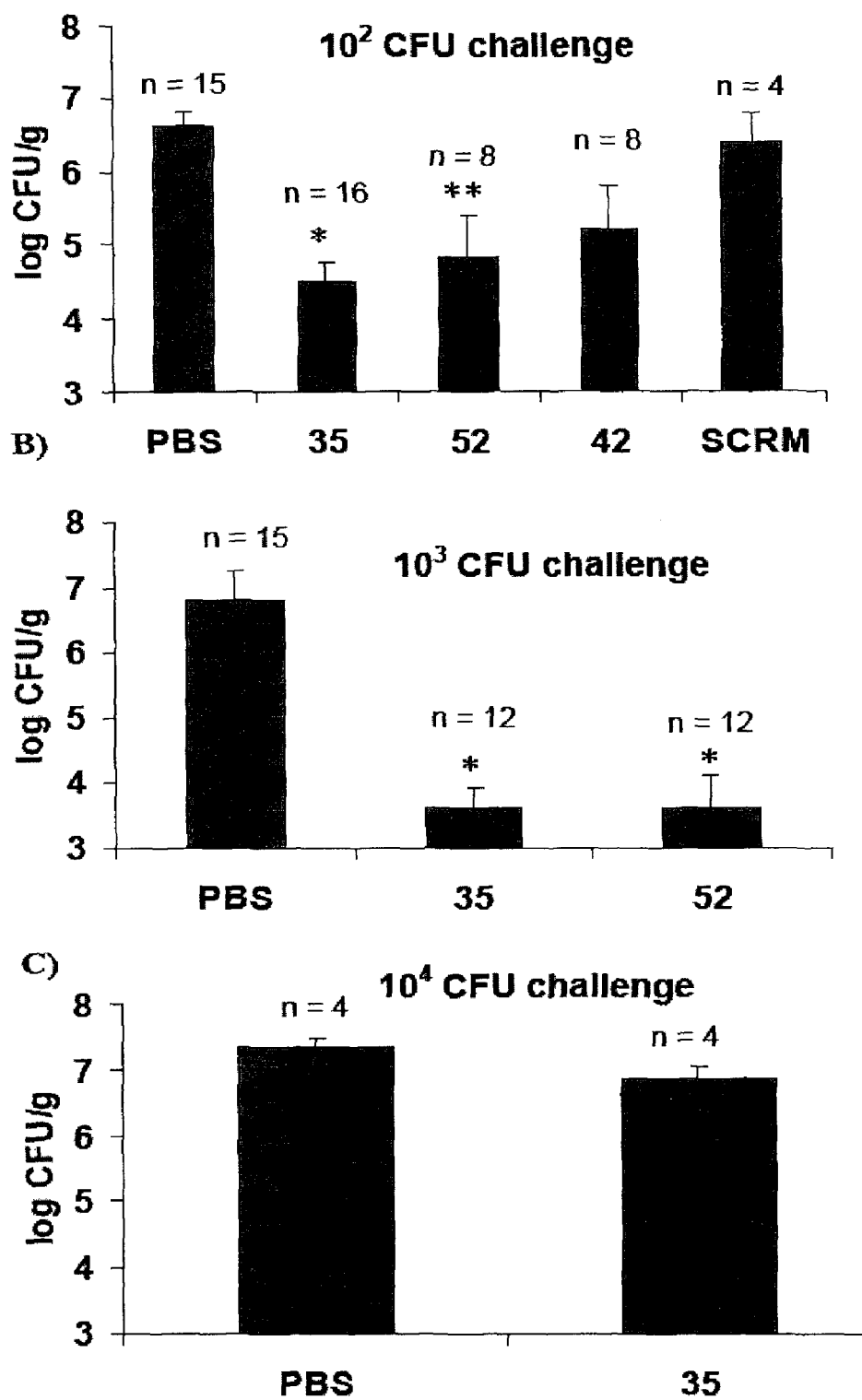
FIG. 4: Effect of hyaluronic acid binding peptide BP treatment on surgical wound infection caused by *S. aureus*.

Mouse model of *S. aureus* wound infection. Mice (C57BL6, male, 6-8 wk old) were obtained from Jackson Laboratories (Bar Harbor, Me.). Groups of mice (N=4/group/experiment) were anesthetized with 100 mg/kg ketamine and 10 mg/kg xylazine, their right thighs were shaved, and the surgical area was disinfected with iodine and 70% ethanol. An incision was made in the skin to expose the thigh muscle, and a 1-cm incision was made with a scalpel into the thigh muscle to the depth of the bone. The muscle was then closed with one 4-0 silk suture, and 10 µl of a *S. aureus* suspension ranging in dose from $10^2$ to $10^4$ CFU was introduced into the incision under the suture. The skin was closed with four additional Prolene sutures. The mice were euthanized at 3 days post-surgery. The wounded muscle tissue was excised, weighed (~0.08 g), and homogenized in 1 ml of tryptic soy broth. Serial dilutions of the homogenates were plated in duplicate and results were expressed as CFU/g tissue. Peptides were administered to animals in two ways. For most experiments, HABPs were solubilized in PBS and administered with a pipet into the wound in a 10 µl volume following challenge with bacteria. A 100 µg dose was used for most experiments. For therapeutic studies, peptide was administered via a 1 ml tuberculin syringe fitted with a 25 gauge needle in a 0.25 ml volume injected into the thigh muscle containing the wound distal from the incision site. Administration of HABP35, HABP52, or HABP42 (100 µg) to the wounds of mice at the time of challenge with $10^2$ CFU resulted in a decrease in bacterial burden at the wound site 3 days later compared with treatment with PBS (FIG. 4A). Treatment with HABP35 or HABP52 resulted in a significant decrease (p<0.0001 and p<0.01, respectively compared with the PBS control). Treatment with the SCRM control peptide did not have this effect.

Treatment of mice with HABP35 or HABP52 was also effective against challenge with a ten-fold higher inoculum ($10^3$ CFU) compared with the PBS control (FIG. 4B). Quantitative culture of mice challenged with this inoculum and with PBS resulted in ~$10^7$ CFU/g tissue, whereas treatment with HABP35 or HABP52 yielded a ~3 log reduction in bacterial numbers. In contrast, treatment with HABPBP35 did not have this effect when an inoculum of $10^4$ CFU was employed. Treatment with this peptide did not reduce bacterial counts in wounds compared with PBS treatment of these animals (FIG. 4C).

Figure 5:
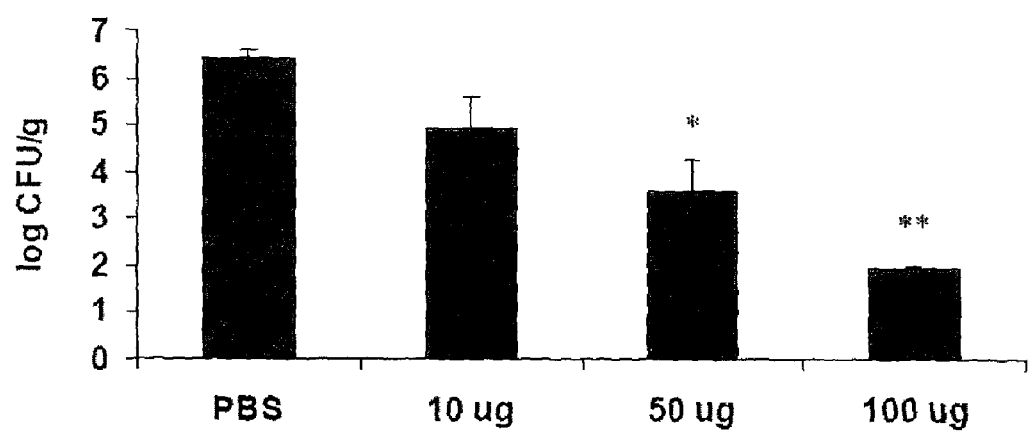
FIG. 5: Dose response of HABP35 treatment of surgical wound infections.

Dose response of HABP treatment. The effect of HABP dose was determined in the next series of experiments. Mice were treated with 10, 50, or 100 µg of HABP35 at the time of challenge with $10^2$ CFU *S. aureus* (FIG. 5). Treatment with 50 or 100 µg was the most effective in reducing bacterial burden (50 µg dose vs. PBS, p<0.005, 100 µg dose vs. PBS, p<0.0001). However, this activity waned when a 10 µg dose was used.

Effect of therapeutic treatment with HABP35. The ability of BP35 to reduce the extent of wound infection in mice when administered 2 or 6 h following challenge was determined. In these experiments, HABP35 (100 µg) was administered via a 25 gauge syringe (0.25 ml) into the thigh muscle containing the sutured incision, but outside of the incision itself. The peptide or PBS was administered at the time of challenge (t=0 h), two, or six hours following challenge (t=2 or 6 h). Administration of the peptide at the time of challenge resulted in a significant decrease in bacterial counts in the wound (FIG. 5A, p<0.001 compared with PBS treatment). This demonstrated that administration of the peptide distal to the incision itself had a similar effect as placing the peptide directly into the wound with a pipet.

Figure 6:
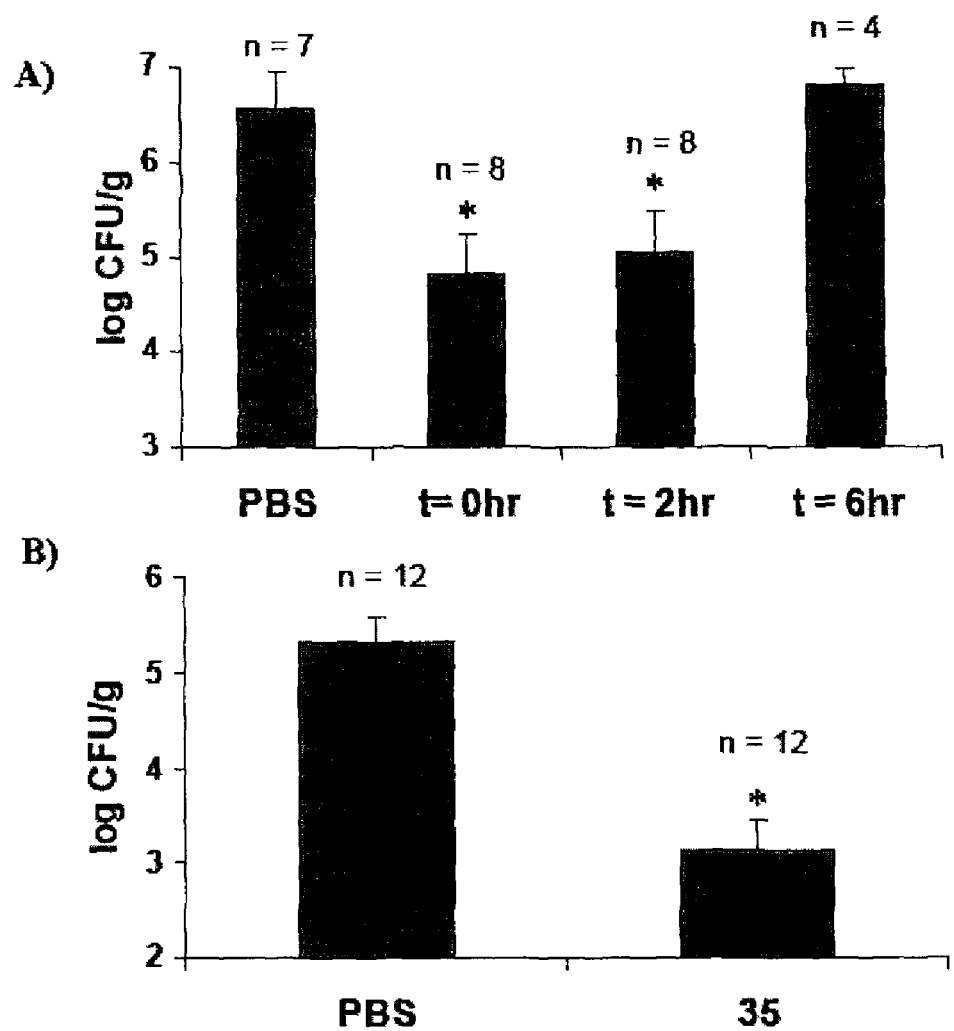
FIG. 6: Effect of therapeutic treatment and activity against MRSA (Methecillin-Resistant *Staphylococcus aureus*) infection.

Treatment with HABP35 two hours following challenge also resulted in a significant reduction in bacterial burden in the wound (FIG. 6A, p<0.001 compared to PBS). In contrast, treatment with HABP35 at t=6 h did not result in reduction in bacterial counts. These data demonstrated that treatment with a BP could be effective when given in a therapeutic mode.

HABP treatment ameliorates wound infection caused by MRSA. The ability of HABP35 to ameliorate wound infection caused by an antibiotic resistant strain of *S. aureus*, MRSA strain Col, was assessed in the model. Mice were challenged with $10^2$ CFU of this strain and treated at the time of challenge with HABP35 (100 µg). For these experiments, HABP35 was directly inoculated into the incision following challenge. Treatment with HABP35 significantly reduced the bacterial burden in the wound (FIG. 6B, p<0.001) by approximately 2 logs compared with PBS-treated control animals.

Gross pathology and histologic analysis of host response. Gross pathologic examination of animals challenged with $10^2$ CFU *S. aureus* and treated with PBS revealed a purulent inflammatory response localized around the suture site. In contrast, mice treated with HABP35 (100 µg) exhibited much less inflammation. Histological examination of these wounds confirmed these findings. Muscle tissue was harvested from mice at designated intervals post-surgery, fixed in 10% buffered formalin, and mounted in paraffin; 5 to 6-µm sections were cut and stained with hematoxylin and eosin for microscopic examination. PBS-treated wounds exhibited a massive inflammatory cell infiltrate at the suture site that extended into the surrounding muscle. The cellular infiltrate was primarily comprised of PMNs and fibrin. Treatment with HABP35 resulted in significantly fewer PMNs infiltrating to the wound site with less fibrin deposition.

Statistical analyses. All animal experiments were performed at least two times and the data pooled. Comparison of *S. aureus* CFU/g tissue was made by the Welch modification of the unpaired Student t test (InStat, GraphPad Software, San Diego, Calif.).

The invention claimed is:

1. A method of inhibiting a *Staphylococcus* infection comprising contacting the *Staphylococcus* bacteria with an inhibiting effective amount of a peptide having the amino acid sequence LKQKIKHVVKLKVVVKLRSQLVKRKQN (SEQ.ID.NO.7); or amidated derivatives or D- isomers thereof.

2. The method of claim 1, wherein the contacting comprises a peptide in combination with at least one antibiotic.

3. A method for the treatment of a *Staphylococcus* infection in humans or animals, comprising administering to a human or animal in need thereof a compound comprising a peptide having the amino acid sequence LKQKIKHVVKLKVVVKLRSQLVKRKQN (SEQ.ID.NO.:7); or amidated derivatives or D- isomers thereof.

4. The method of claim 3, wherein the administration is subcutaneous or intramuscular.

5. The method of claim 3, wherein the administration comprises a peptide in combination with at least one antibiotic.

6. A formulation for inhibiting a *Staphylococcus* infection comprising a peptide having the amino acid sequence LKQKIKHVVKLKVVVKLRSQLVKRKQN (SEQ.ID.NO.:7); and a antimicrobial agent.

7. The formulation of claim 6, wherein said antimicrobial agent is an antibiotic.

8. A method for providing protection from a *Staphylococcus* infection in humans or animals, comprising administering to a human or animal in need thereof an effective amount of a peptide having the amino acid sequence LKQKIKHVVKLKVVVKLRSQLVKRKQN (SEQ.ID.NO.:7); or an amidated derivative or D- isomer thereof.

9. The method of claim 8 wherein the peptide is administered in combination with at least one antibiotic.

10. The method of claim 8 wherein the peptide is administered subcutaneously or intramuscularly.

* * * * *

SEQUENCE LISTING

<160> NUMBER OF SEQ ID NOS: 13

<210> SEQ ID NO 1
<211> LENGTH: 15
<212> TYPE: PRT
<213> ORGANISM: artificial
<220> FEATURE:
<223> OTHER INFORMATION: HA binding peptide of formula I

<400> SEQUENCE: 1

Thr Met Thr Arg Pro His Phe His Lys Arg Gln Leu Val Leu Ser
1               5                   10                  15

<210> SEQ ID NO 2
<211> LENGTH: 15
<212> TYPE: PRT
<213> ORGANISM: artificial
<220> FEATURE:
<223> OTHER INFORMATION: HA binding peptide of formula II

<400> SEQUENCE: 2

Ser Thr Met Met Ser Arg Ser His Lys Thr Arg Ser Cys His His
1               5                   10                  15

<210> SEQ ID NO 3
<211> LENGTH: 14
<212> TYPE: PRT
<213> ORGANISM: artificial
<220> FEATURE:
<223> OTHER INFORMATION: HA binding peptide of formula III

<400> SEQUENCE: 3

Ser Thr Met Met Ser Arg Ser His Lys Thr Arg Ser His His
1               5                   10

<210> SEQ ID NO 4
<211> LENGTH: 15
<212> TYPE: PRT
<213> ORGANISM: artificial
<220> FEATURE:
<223> OTHER INFORMATION: HABP01 - HA binding peptide of formula III

<400> SEQUENCE: 4

Ser Thr Met Met Ser Arg Ser His Lys Thr Arg Ser His His Val
1               5                   10                  15

<210> SEQ ID NO 5
<211> LENGTH: 15
<212> TYPE: PRT
<213> ORGANISM: artificial
<220> FEATURE:
<223> OTHER INFORMATION: scrambled sequence of HABP01

<400> SEQUENCE: 5

His Lys Ser Val Ser Arg His Thr Ser Met Arg His Ser Thr Met
1               5                   10                  15

<210> SEQ ID NO 6
<211> LENGTH: 14
<212> TYPE: PRT
<213> ORGANISM: artificial
<220> FEATURE:
<223> OTHER INFORMATION: HA binding peptide based on human RHAMM HA
      binding domains

<400> SEQUENCE: 6

Val Ser Lys Leu Arg Ser Gln Leu Val Lys Arg Lys Gln Asn
1               5                   10

<210> SEQ ID NO 7
<211> LENGTH: 27
<212> TYPE: PRT
<213> ORGANISM: artificial
<220> FEATURE:
<223> OTHER INFORMATION: HA binding peptide having two HA binding
      domains

<400> SEQUENCE: 7

Leu Lys Gln Lys Ile Lys His Val Val Lys Leu Lys Val Val Val Lys
1               5                   10                  15

Leu Arg Ser Gln Leu Val Lys Arg Lys Gln Asn
            20                  25

<210> SEQ ID NO 8
<211> LENGTH: 15
<212> TYPE: PRT
<213> ORGANISM: artificial
<220> FEATURE:
<223> OTHER INFORMATION: All d-isomer version of HABP01

<400> SEQUENCE: 8

Ser Thr Met Met Ser Arg Ser His Lys Thr Arg Ser His His Val
1               5                   10                  15

<210> SEQ ID NO 9
<211> LENGTH: 16
<212> TYPE: PRT
<213> ORGANISM: artificial
<220> FEATURE:
<223> OTHER INFORMATION: HA binding peptide

<400> SEQUENCE: 9

Gly Ala His Trp Gln Phe Asn Ala Leu Thr Val Arg Gly Gly Gly Ser
1               5                   10                  15

<210> SEQ ID NO 10
<211> LENGTH: 12
<212> TYPE: PRT
<213> ORGANISM: artificial
<220> FEATURE:
<223> OTHER INFORMATION: HABP52 sequence

<400> SEQUENCE: 10

Gly Ala His Trp Gln Phe Asn Ala Leu Thr Val Arg
1               5                   10

<210> SEQ ID NO 11
<211> LENGTH: 12
<212> TYPE: PRT
<213> ORGANISM: artificial
<220> FEATURE:
<223> OTHER INFORMATION: HABP52 sequence

<400> SEQUENCE: 11

Gly Ala Ala Trp Gln Phe Asn Ala Leu Thr Val Arg
1               5                   10

<210> SEQ ID NO 12
<211> LENGTH: 12
<212> TYPE: PRT
<213> ORGANISM: artificial
<220> FEATURE:
<223> OTHER INFORMATION: HABP52 sequence

```
<400> SEQUENCE: 12

Gly Ala His Trp Gln Phe Ala Ala Leu Thr Val Arg
1               5                   10

<210> SEQ ID NO 13
<211> LENGTH: 12
<212> TYPE: PRT
<213> ORGANISM: artificial
<220> FEATURE:
<223> OTHER INFORMATION: HABP52  sequence

<400> SEQUENCE: 13

Gly Ala His Trp Gln Phe Asn Ala Leu Thr Val Ala
1               5                   10
```